(12) United States Patent
Bhattacharyya et al.

(10) Patent No.: US 10,703,700 B2
(45) Date of Patent: Jul. 7, 2020

(54) LIQUID PHASE OXIDATION OF LOWER ALKANES TO OXYGENATES

(71) Applicant: UOP LLC, Des Plaines, IL (US)

(72) Inventors: Alakananda Bhattacharyya, Glen Ellyn, IL (US); Joel T. Walenga, Lake Zurich, IL (US); Nina I. Kuznetsova, Novosibirsk (RU)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/685,531

(22) Filed: Aug. 24, 2017

(65) Prior Publication Data
US 2019/0062247 A1     Feb. 28, 2019

(51) Int. Cl.
| | | |
|---|---|---|
| *C07C 45/33* | (2006.01) | |
| *B01J 31/22* | (2006.01) | |
| *C07C 29/50* | (2006.01) | |
| *C07C 67/39* | (2006.01) | |
| *B01J 31/04* | (2006.01) | |
| *C07C 27/12* | (2006.01) | |

(Continued)

(52) U.S. Cl.
CPC ............. *C07C 45/33* (2013.01); *B01J 31/006* (2013.01); *B01J 31/0247* (2013.01); *B01J 31/0279* (2013.01); *B01J 31/0298* (2013.01); *B01J 31/04* (2013.01); *B01J 31/2226* (2013.01); *B01J 31/2234* (2013.01); *C07C 27/12* (2013.01); *C07C 29/50* (2013.01); *C07C 67/39* (2013.01); *B01J 2231/70* (2013.01); *B01J 2531/72* (2013.01); *B01J 2531/845* (2013.01)

(58) Field of Classification Search
None
See application file for complete search history.

(56) References Cited

U.S. PATENT DOCUMENTS 3,293,292 A * 12/1966 Olivier .................. C07C 51/215
                                                           560/231
4,131,741 A    12/1978 Bartlett et al.
(Continued)

FOREIGN PATENT DOCUMENTS

| EP | 0126488 B1 | 4/1986 |
| EP | 0824962 B1 | 7/2003 |

OTHER PUBLICATIONS

Partenheimer ("Chapter 7: Nature of the Co—Mn—Br Catalyst in the Methylaromatic Compounds Process" Catalytic Selective Oxidation ACS Symposium Series; American Chemical Society; vol. 523, 1993, p. 81-88) (Year: 1993).*

(Continued)

*Primary Examiner* — Amy C Bonaparte (57) ABSTRACT

A liquid phase selective oxidation process is described. The process involves the partial oxidation of alkanes to partially oxidized products. A lower alkane, a solvent, and a soluble metal catalyst are contacted in the presence of an oxidizing agent in a reaction zone under partial oxidation conditions to produce the partially oxidized products. The partially oxidized products include one or more of lower alkyl alcohols, lower alkyl ketones, and lower alkyl acetates. The soluble metal catalyst is a soluble metal salt of cobalt, manganese, chromium, titanium, copper, nickel, vanadium, iron, molybdenum, tin, cerium, zirconium, or combinations thereof, and the promoter comprises a bromine source, an imide source, or combinations thereof.

19 Claims, 1 Drawing Sheet

(51) Int. Cl.
B01J 31/02 (2006.01)
B01J 31/00 (2006.01)

(56) References Cited

U.S. PATENT DOCUMENTS

| | | | |
|---|---|---|---|
| 4,337,356 A | | 6/1982 | Logsdon et al. |
| 4,859,798 A | | 8/1989 | Lyons et al. |
| 5,220,080 A | | 6/1993 | Lyons et al. |
| 5,409,876 A | | 4/1995 | Clerici et al. |
| 6,037,507 A | * | 3/2000 | Nakano .................. C07C 29/50 502/161 |
| 6,137,001 A | | 10/2000 | Broeker et al. |
| 6,555,715 B1 | * | 4/2003 | Kocal ....................... C07C 1/24 502/155 |
| 6,670,509 B1 | * | 12/2003 | Kurek ..................... C07C 45/33 568/320 |
| 7,214,837 B2 | | 5/2007 | Deshpande et al. |
| 7,456,313 B2 | | 11/2008 | Lemonds et al. |
| 7,692,036 B2 | | 4/2010 | Wonders et al. |
| 2006/0116530 A1 | * | 6/2006 | Wonders ................. C07C 51/21 562/412 |
| 2007/0149832 A1 | * | 6/2007 | Chen ...................... C07C 29/095 568/910 |
| 2008/0249198 A1 | * | 10/2008 | Chen ...................... C07C 29/095 518/703 |
| 2012/0201743 A1 | | 8/2012 | Chadwick et al. |

OTHER PUBLICATIONS

Frusteri et al, Liquid-Phase Selective Oxidation of Propane on Silica-Supported Nafion Catalysts, Journal of Natural Gas Chemistry 11(2002)180{185.

Corresponding Russian Application No. 2015136222 filed Aug. 26, 2015.

* cited by examiner

LIQUID PHASE OXIDATION OF LOWER ALKANES TO OXYGENATES

BACKGROUND OF THE INVENTION

Processes for the selective oxidation of lower alkanes to oxygenates are known.

Some processes involve the oxidation of alkanes to carboxylic acids. For example, U.S. Pat. No. 4,131,741 describes the production of oxygenated organic compounds such as acetic acid by oxygenating a $C_3$ to $C_7$ saturated aliphatic hydrocarbon in the liquid phase with molecular oxygen in the presence of an inert reaction medium and a cobalt catalyst. The process is designed to minimize the reduction of $Co^{+3}$ to $Co^{+2}$. In this process, the butane to oxygen weight ratio is 3.4:1. No promoter is used. The '741 patent contrasts its process with processes using promoters and states that the induction period can be substantially eliminated during batch operation with or without catalyst recycle and continuous operation maintained without the addition or recycle of a promoter when not less than 5% and not more than 90% of the cobalt is in the +3 oxidation state.

U.S. Pat. No. 4,337,356 describes the continuous cobalt catalyzed liquid-phase oxidation of butane to acetic acid. This process used ethanol, methyl ethyl ketone and ethanol, and acetaldehyde as promoters. The water concentration, the iron concentration, and the succinic acid concentration in the catalyst recycle stream are carefully controlled, as is the oxygen concentration in the reactor effluent. The iron concentration is limited to less than 1000 ppm because higher amounts are said to kill the oxidation of butane. The iron comes from corrosion of the stainless steel reaction system.

U.S. Pat. No. 4,859,798 discusses the liquid phase oxidation of alkanes at relatively low temperatures using heteropolyacids or polyoxoanions promoted with azide or certain metals.

EP 0 126 488 describes a process for the liquid phase oxidation of $C_3$ to $C_{13}$ alkanes using oxygen, a cobalt catalyst, and a catalyst promoter such as acetaldehyde at elevated temperature and pressure. The process can be controlled to make specified products such as carboxylic acids, dialkyl ketones, alkyl esters, and alkanols.

U.S. Pat. No. 7,456,313 involves the liquid phase oxidation of hydrocarbons in the presence of an oxidation catalyst to form an oxidation product. The process is performed in the presence of solvent having a boiling point of at least 25° C. and Hildebrand solubility parameter no greater than 14 $MPa^{1/2}$. The catalyst is either a solid heterogeneous mixed metal oxide catalyst or a liquid catalyst dissolved in the solvent. The solvent can be a fluorinated organic compound, selected silicones or siloxanes and silicone or siloxane polymers, and hydrophobic ionic liquids.

Other processes for the conversion of alkanes to alcohols and ketones involve the use of solid catalysts. For example, U.S. Pat. No. 7,214,837 teaches a process for the production of a mixture of alcohols and ketones by the liquid phase oxidation of higher alkanes using a catalyst system consisting of transition group metals and a support in the presence of alkyl hydroperoxide.

US 2012/0201743 describes a process for preparing oxygenate products by direct conversion of $C_1$ to $C_3$ alkanes in the gas or liquid phase. The alkanes are contacted with hydrogen peroxide or a hydroperoxy species in the presence of a gold-based heterogeneous catalyst on a metal oxide support in the form of nanotubes, nanofibers, nanowires, or nanorods.

However, solid catalysts are generally less active and less selective, and they may promote the formation of acid-which is not desirable for the production of alcohols or other partially oxidized products.

Current alkane dehydrogenation technology which converts alkanes to alcohols operates at high temperatures and has high capital and operating costs. For example one process utilizes a heterogeneous solid catalyst containing platinum and operates at high temperatures, e.g., above 550° C.

Therefore, there is a need for a process for converting alkanes to alcohols which does not use expensive catalysts and which does not operate at high temperatures.

SUMMARY OF THE INVENTION

The present invention involves a liquid phase selective oxidation process. In one embodiment, the process involves the partial oxidation of alkanes to partially oxidized products. A lower alkane, a solvent, a soluble metal catalyst, and a promoter are contacted in the presence of an oxidizing agent in a reaction zone under partial oxidation conditions to produce the partially oxidized products. The partially oxidized products include one or more of lower alkyl alcohols, lower alkyl ketones, and lower alkyl acetates. The ratio of the lower alkane to oxygen is in a range of about 20:1 to about 1:2. The soluble metal catalyst is a soluble metal salt of cobalt, manganese, chromium, titanium, copper, nickel, vanadium, iron, molybdenum, tin, cerium, zirconium, or combinations thereof, and the promoter comprises a bromine source, an imide source, or combinations thereof.

DETAILED DESCRIPTION OF THE INVENTION

Figure 1:
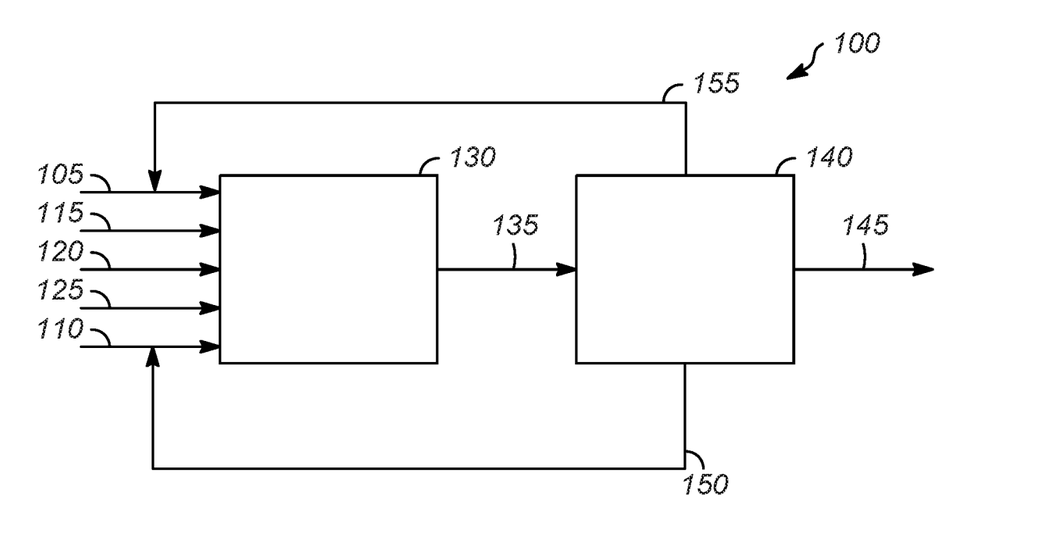
The FIGURE is a general process flow diagram for one embodiment of a partial oxidation process of the present invention.

The present invention involves a liquid phase process in which lower alkanes are oxidized selectively to oxygenates. The oxygenates produced can be further reacted to produce olefins or other value-added products.

The process is a liquid phase selective oxidation process. A lower alkane, a solvent, and a liquid phase catalyst are contacted in the presence of an oxidizing agent in a reaction zone under partial oxidation conditions. By lower alkane, we mean an alkane having 1 to 8 carbon atoms. The partial oxidation produces partially oxidized products comprising one or more of lower alkyl alcohols, lower alkyl ketones, and lower alkyl acetates. The lower alkyl alcohols, lower alkyl ketones, and lower alkyl acetates have 1 to 8 carbon atoms.

The reaction takes place at lower temperature than the prior art process using the heterogeneous solid oxide catalyst. In addition, the process provides higher product yield and has lower capital costs the prior art process using the heterogeneous solid oxide catalyst.

One example of the reaction is the liquid phase oxidation of propane to propanol or isopropanol. Although other oxidation products might be formed, such as acetone, CO, and CON, if the selectivity of propanol is high, the propanol can be dehydrated to form propylene.

The FIGURE illustrates one embodiment of the process 100. The lower alkane feed stream 105, the solvent stream 110, the liquid phase catalyst stream 115, the oxidizing agent stream 120, and the optional promoter stream 125 are introduced into the reaction zone 130. Although these are shown as separate streams, it will be understood that one or more of the streams can be combined with other streams.

The lower alkane comprises an alkane having 1 to 8 carbon atoms, or 2 to 5 carbon atoms.

The solvent can comprise a carboxylic acid, acetonitrile, benzyl nitrile, or combinations thereof. The carboxylic acid desirably has from 1 to 7 carbon atoms. In an embodiment, the carboxylic acid comprises acetic acid. The solvent may contain more than one carboxylic acid. For example, the solvent may comprise benzoic acid. In another embodiment, the carboxylic acid of the solvent is acetic acid.

The catalyst comprises at least one of cobalt, manganese, chromium, titanium, copper, nickel, vanadium, iron, molybdenum, tin, cerium and zirconium. In an embodiment, the catalyst comprises cobalt and manganese. The metal may be in the form of an inorganic or organic salt or compound, such as, but not limited to acetates, bromides, and acetyl acetonates of Co, Mn, Cr, Ti, Cu, Ni, V, Fe, Mo, Sn, Ce, and/or combinations thereof. For example, the metal catalyst may be in the form of a carboxylic acid salt, such as a metal acetate and hydrates thereof. Exemplary catalysts include cobalt (III) acetate, cobalt (III) acetylacetonate, cobalt (II) acetate, and manganese (II) acetate, individually or in combination such as a mixture of Co(II or III) acetate or acetylacetonate and Mn(II) acetate or acetylacetonate. Another catalyst class are polyoxometalates such as $H_5PMo_{10}V_2O_{40}$. The amount of catalyst metal used in the invention may vary widely. For example, the amount of cobalt metal may range from about 0.01 wt % to about 1 wt % relative to the weight of the solvent, or about 0.02 wt % to about 0.5 wt %, or about 0.05 wt % to about 0.2 wt %. The amount of manganese may range from about 0 wt % to about 1 wt % relative to the weight of the solvent, or about 0.02 wt % to about 0.5 wt %, or about 0.05 wt % to about 0.2 wt %. When a combination of cobalt and manganese is used as the catalyst, the weight ratio of cobalt to manganese is typically in the range of 5:1 to 1:5, and preferably 2:1 to 1:2.

The promoter can be a bromine source, an imide source, or combinations thereof. Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono and di-bromoacetic acid, bromoacetyl bromide, tetrabromoethane, ethylene di-bromide, butyl-methylimidizoliumbromide, and tetrabutylammonium bromide. In an embodiment, the bromine source comprises, or consists essentially of, or consists of, hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the solvent. The solvent includes the carboxylic acid, and the optional water.

It is believed that the reaction involves a radical chain mechanism and the formation of hydroperoxides. The decomposition of the hydroperoxides gives stable alcohols and ketones. Ketones can also be formed by the oxidation of the alcohols. The reactions believed to be involved are as follows:

$$Br + Co^{3+} = Br\cdot + Co^{2+}$$

$$RH + Br\cdot = R\cdot + HBr$$

$$R\cdot + O_2 = RO_2\cdot$$

$$RO_2\cdot + RH \rightarrow ROOH + R\cdot$$

$$ROOH = RO\cdot + HO\cdot$$

$$RO\cdot + RH = ROH + R\cdot$$

$$RO_2\cdot + ROOH = ROH + RO\cdot + O_2$$

$$Co^{2+} + Mn^{3+} = Co^{3+} + Mn^{2+}$$

A similar radical chain mechanism would occur using the imide promoter. Imide sources include but are not limited to, N-hydroxyphthalimide (NHPI). NHPI is used to generate corresponding radicals similar to that shown above for the radical reaction involving Br. The amount of imide typically ranges from about 0.01 wt % to about 2 wt %, relative to the weight of the solvent, or about 0.05 wt % to about 1 wt %, or about 0.1 wt % to about 1 wt %.

The process has better selectivity control than the prior art processes discussed above.

Suitable oxidizing agents for the process provide a source of oxygen atoms to oxidize the lower alkane at the partial oxidation conditions employed. Examples of oxidizing agents include oxygen-containing gases, peroxides, superoxides, and nitrogen compounds containing oxygen such as nitrous oxide and any of the other oxides of nitrogen. In an embodiment, the oxidizing agent is a gas comprising oxygen, e.g. air, carbon dioxide, and molecular oxygen. The gas may be a mixture of gases. Typically, the oxygen is added as a mixture of oxygen and an inert second gas such as nitrogen or helium. The oxygen level in this mixture will typically range from about 5 vol % to about 21 vol %, but in some cases may be as high as about 50 vol %.

In some embodiments, the weight ratio of the lower alkane to oxygen at the start of the reaction is in a range of about 50:1 to about 2:1, or about 25:1 to about 2:1, or about 20:1 to 2:1, or about 10:1 to about 2:1, or about 20:1 to about 3:1, or about 20:1 to about 5:1, or about 20:1 to about 7:1, or about 20:1 to about 10:1. In some embodiments, the weight ratio of solvent to oxygen at the start of the reaction is in the range of about 500:1 to about 25:1, or 300:1 to 20:1, or 250:1 to 20:1. In some embodiments, at the start of the reaction the weight ratio of solvent to alkane is in the range of about 50:1 to about 1:1, or 50:1 to 2:1, or 20:1 to 3:1, or 20:1 to 5:1. In all cases, ratios that would result in explosive conditions should be avoided.

The lower alkane feed stream 105, the solvent stream 110, the liquid phase catalyst stream 115, the oxidizing agent stream 120, and the optional promoter stream 125 are contacted in the reaction zone 130. The lower alkane is partially oxidized to the partial oxidation products.

The contacting step(s) may be practiced in laboratory scale experiments through full scale commercial operations. The process may be operated in batch, continuous, or semi-continuous mode. The contacting step can take place in various ways. The order of addition of the components (e.g., lower alkane, solvent, bromine source, catalyst, and oxidizing agent) is not critical; however, the oxidizing agent should be added last. For example, the components can be added individually, or two or more components may be combined or mixed before being combined or mixed with other components.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. Nos. 7,692,036 and 6,137,001.

The contacting step[s] takes place under partial oxidation conditions. Suitable oxidizing conditions generally include a temperature in the range of about 40° C. to about 250° C., or about 80° C. to about 200° C., or about 100° C. to about 180° C., or about 120° C. to about 160° C. The pressure is typically in the range of about 0.7 MPa(g) to about 13.8 MPa(g), or about 1 MPa(g) to about 10 MPa(g), or about 1 MPa(g) to about 8 MPa(g), or about 1 MPa(g) to about 7 MPa(g), or about 2 MPa(g) to about 6 MPa(g), or about 2.7 MPa(g) to about 7 MPa(g). The residence time ranges from about 1 min to about 360 min, or about 10 min to about 180 min.

After the reaction is completed, the effluent 135 can be sent to the separation zone 140 where the partially oxidized product 145 is separated from the solvent 150 and the unreacted lower alkane 155. The solvent 150 can be recycled to the reaction zone 130 and combined with the solvent stream 110. The catalyst and/or the promoter can be recycled separately or with the solvent 150, if desired. The unreacted lower alkane 155 can be recycled to the reaction zone 130. The separation can be done using any suitable process, including, but not limited to, distillation, decantation, absorption, and desorption.

The partially oxidized products include, but are not limited to, lower alkyl alcohols, lower alkyl ketones, and lower alkyl acetates. The lower alkyl alcohols, lower alkyl ketones, and lower alkyl acetates have 1 to 8 carbon atoms, or 3 to 5 carbon atoms. In some embodiments, the process produces minimal amounts of monocarboxylic acids or dicarboxylic acids. By minimal amounts, we mean less than about 10 wt % of monocarboxylic acids and dicarboxylic acids, or less than about 8 wt %, or about 6 wt %, or less than about 5 wt %.

The selectivity to the desirable partially oxidized products (e.g., for propane oxidation, the desirable products are isopropyl alcohol, propyl alcohol, isopropyl acetate, propyl acetate, and acetone) is typically at least about 35 mol %, or at least about 40 mol %, or at least about 45 mol %, or at least about 50 mol %, or at least about 55 mol %, or at least about 60 mol %, or at least about 65 mol %, or at least about 70 mol %, or at least about 75 mol %, or at least about 80 mol %, or at least about 85 mol %. Using propane as an example, the selectivity is calculated by summing to total moles of the $C_3$ oxygenates+$CO_x/3$+methyl acetate/3 produced to get an estimate of the total moles of propane converted. ($CO_x$ and methyl acetate are divided by three because one mole propane can make three of each (assuming methyl acetate is formed by reacting methanol with acetic acid).) The molar amounts of the individual products (acetone, isopropyl alcohol, COx, etc.) are then divided by the total moles of propane converted and multiplied by 100 to get an estimate of the percent selectivity.

In this process, about 100% of the oxygen is utilized when a large excess of feed is used to make oxygenates with low selectivity to $CO_x$. The selectivity to $CO_x$ is typically less than about 25%, or less than about 20%, or less than about 15%, or less than about 10%.

Examples (1 to 39)

The solvent (typically acetic acid), catalyst (typically $Co^{3+}$, or $Co^{2+}$), bromide or imide promoter, and other additives (such as tert-butyl hydroperoxide (TBHP) initiator, and methylimidazole (MIm) to modify the solvent) as shown in Tables 1-4 were added to the high pressure titanium Parr reactor equipped with a gas entrainment stirrer (to recycle gas back to the liquid) (450 ml for Examples 1-13, 300 ml for Examples 14-32, and 335 ml for Examples 333-39) at room temperature. The reactor was purged with nitrogen, and the nitrogen was then vented. Propane was added at room temperature, followed by the oxidizing agent, typically air. The resulting reactor pressure was dependent on the amount of alkane and oxidizing agent added and the temperature of the reaction, but additions and temperatures used were designed to operate within the maximum operating pressures and temperatures of the reactor used. The temperatures are shown in Tables 1-4. Pressures typically ranged from 2.8 MPa(g) to 6.9 MPa(g) (400 to 1000 psig) at the operating temperature. Higher temperatures and pressures would be possible if a reactor with a higher pressure rating were used. The reaction mixture was then stirred at about 350 rpm until the pressure stabilized, typically about 10 min. The reaction mixture was heated to the reaction temperature (see tables), which took about 30 min. During the heat up and throughout the test, the stirring rate was increased to about 1600 rpm. The reactor was run at the reaction temperature for the desired length of time (see tables). During the test the reactor was cooled (using external cooling air) or heated (using reactor heater) as necessary to maintain the desired reaction temperature. At the end of the test, the reactor was cooled to room temperature using cooling air until it reached a temperature less than about 80° C., then it was placed in cooling water to cool to room temperature. Cooling generally took about 30 min. After cooling, the reaction products were analyzed using gas chromatography. The wt % conversion for $C_3H_8$ and $O_2$ was calculated by subtracting the difference between the pre-reaction and post-reaction propane or oxygen, dividing by the pre-reaction propane or oxygen, then multiplying by 100.

Examples 1-13 (Table 1) show the oxidation of propane in the presence of cobalt acetate and/or manganese acetate catalysts with acetic acid solvent, and with and without HBr as the promoter. The results show very efficient oxygen conversion, nearly 100%. The propane conversion was limited based on oxygen availability. The COx selectivity was good; it was generally in the range of 5 to 25% (low selectivity for Cox is desirable). The desirable $C_3$ oxygenate selectivity ranged from 40% to as high as close to about 90% by volume. Methyl acetate selectivity goes down and acetone selectivity goes up in the presence of HBr.

Examples 14-17 (Table 2) show the oxidation of propane in the presence of cobalt (II) acetate catalysts with acetic acid solvent, with different Br promoters. There are no marked differences between the various bromine sources in oxygen conversion or in $C_3$ oxygenates selectivity.

Examples 18-32 (Table 3) show the oxidation of propane in the presence of cobalt (II) acetate catalyst and NHPI as the promoter. TBHP was added as an initiator. Various additives were included as shown in Table 3. In Example 29, a heterogeneous mixed metal oxide oxidation catalyst, $H_5PMo_{10}V_2O_{40}$, was used in place of cobalt (II) acetate. TBHP allows the oxidation of propane at 110-120° C. The polyoxometalate catalyst enhances undesirable COx selectivity at the expense of desirable $C_3$ oxygenate selectivity.

Examples 33-39 (Table 4) show the oxidation of propane in the presence of cobalt (II) acetate catalyst (0.1 g) and NHPI (0.1 g) as the promoter, with acetic acid solvent (50 g), and without TBHP. If TBHP is not included, the temperature needs to be increased to obtain conversion and selectivities similar to those with TBHP. This observation is reasonable as TBHP is a peroxide and hence initiates the oxidation as discussed before.

TABLE 1

| Test | Solvent | Catalyst | Temp. °C. | Time, min | Initial mmol C$_3$H$_8$ | Initial mmol O$_2$ | Conversion, % C$_3$H$_8$ | Conversion, % O$_2$ | Selectivity to C$_3$ Desirable Products, % AC | IPA | PA | IPAc | PAc | Sum C$_3$ Oxygenates | Selectivity to Other Products MAc | CO$_x$ |
|---|---|---|---|---|---|---|---|---|---|---|---|---|---|---|---|---|
| 1 | 150 g HOAc | 0.9 g Co(AcAc)3$^a$ | 160 | 120 | 238 | 50 | 8.0 | 99 | 22.5 | 1.6 | 0.0 | 10.8 | 1.6 | 36.4 | 53.5 | 10.1 |
| 2 | 150 g HOAc + 0.2 g HBr | 0.9 g Co(AcAc)3 | 160 | 120 | 238 | 50 | 8.8 | 99 | 58.9 | 1.4 | 0.0 | 12.5 | 1.0 | 73.8 | 15.8 | 10.4 |
| 3 | 150 g HOAc + 0.3 g HBr | 0.9 g Co(AcAc)3 | 160 | 120 | 238 | 50 | 8.9 | 98 | 61.7 | 1.9 | 0.0 | 14.1 | 1.4 | 79.1 | 14.1 | 6.8 |
| 4 | 150 g HOAc + 0.4 g HBr + 2.2 g H$_2$O | 0.6 g Co(OAc)2$^a$ + 0.6 g Mn(OAc)2 Mn(OAc)2 | 160 | 120 | 238 | 50 | 4.6 | 98 | 44.4 | 2.0 | 0.0 | 21.0 | 1.6 | 69.0 | 7.8 | 23.3 |
| 5 | 150 g HOAc + 0.4 g HBr + 0.2 g H$_2$O | 0.4 g Co(OAc)2 + 0.6 g Mn(OAc)2 | 160 | 120 | 238 | 50 | 5.0 | 98 | 42.6 | 1.6 | 0.0 | 20.1 | 5.9 | 70.1 | 11.3 | 18.6 |
| 6 | 150 g HOAc + 0.3 g HBr | 0.9 g Co(AcAc)3 + 0.6 g Mn(OAc)2 Mn(OAc)2 | 160 | 120 | 238 | 50 | 5.1 | 98 | 52.2 | 2.0 | 0.0 | 19.3 | 1.4 | 74.9 | 5.7 | 19.4 |
| 7 | 150 g HOAc + 0.3 g HBr | 0.9 g Co(AcAc)3 + 0.6 g Mn(OAc)2$^a$ | 160 | 120 | 590 | 50 | 3.3 | 98 | 55.0 | 4.9 | 0.0 | 26.4 | 1.8 | 88.1 | 3.6 | 8.3 |
| 8 | 150 g HOAc + 0.4 g HBr | 0.6 g Co(OAc)2 + 0.6 g Mn(OAc)2 | 160 | 120 | 241 | 146 | 15.4 | 99 | 26.4 | 2.3 | 0.0 | 18.9 | 1.7 | 49.3 | 3.2 | 47.5 |
| 9 | 150 g HOAc + 0.3 g HBr + 0.2 g H$_2$O | 0.4 g Co(OAc)2 + 0.4 g Mn(OAc)2 | 150 | 30 | 493 | 52 | 3.4 | 98 | 61.1 | 13.5 | 0.3 | 10.0 | 1.5 | 86.5 | 6.6 | 6.9 |
| 10 | 150 g HOAc + 0.3 g HBr | 0.9 g Co(AcAc)3 | 160 | 120 | 238 | 134 | 24.8 | 97 | 59.8 | 1.0 | 0.0 | 7.9 | 0.9 | 69.7 | 8.8 | 21.5 |
| 11 | 150 g HOAc + 0.3 g HBr | 0.9 g Co(AcAc)3 | 160 | 120 | 238 | 134 | 22.7 | 99 | 65.5 | 2.2 | 0.0 | 9.1 | 1.1 | 77.9 | 9.3 | 12.8 |
| 12 | 150 g HOAc + 0.3 g HBr | 0.9 g Co(AcAc)3 | 160 | 120 | 238 | 112 | 2.0 | 18 | 17.8 | 9.4 | 0.0 | 49.5 | 3.4 | 80.2 | 4.9 | 15.0 |
| 13 | 150 g HOAc + 0.3 g HBr | 0.9 g Co(AcAc)3 | 150 | 30 | 614 | 52 | 3.9 | 98 | 58.8 | 14.0 | 0.6 | 11.0 | 1.9 | 86.3 | 7.8 | 5.9 |

AC - Acetone,
IPA - Isopropyl Alcohol,
PA - Propyl Alcohol,
IPAc - Isopropyl Acetate,
PAc - Propyl Acetate,
MAc - Methyl Acetate
HOAc - acetic acid,
Co(AcAc)3 - cobalt (III) acetylacetonate,
Co(OAc)2 - cobalt (II) acetate,
Mn(OAc)2 - manganese (II) acetate,
C$_3$ = Ac + IPA + PA + IPAc + PAc,
CO$x$ = CO$_2$ + CO

TABLE 2

| | Br-containing additive | Temp., time | Initial, mmol C3H8 | Initial, mmol O2 | Conv., % C3H8 | Conv., % O2 | Selectivity to C3, % Ac | IPA | PA | IPAc | PAc | IPBr | AAc | C3 | Sel. to other prod., % MAc + MA | CO$x$ |
|---|---|---|---|---|---|---|---|---|---|---|---|---|---|---|---|---|
| 14 | 0.1 g bmimBr | 160° C., 60 min | 85 | 6 | 3.2 | 83 | 36.8 | 11.0 | 0.3 | 19.9 | 2.2 | 11.4 | 0.1 | 81.7 | 13.5 | 4.8 |
| 15 | 0.1 g mim + 0.1 g HBr | 150° C., 40 min | 85 | 6 | 3.1 | 87 | 53.8 | 13.1 | 0.4 | 8.5 | 1.4 | 4.2 | 0.2 | 81.6 | 10 | 8.4 |
| 16 | 0.15 g TBABr | 160° C., 60 min | 85 | 6 | 3.0 | 90 | 33.2 | 11.5 | 2.2 | 18.6 | 2.5 | 10.3 | 0.2 | 78.5 | 12.1 | 9.4 |
| 17 | 0.09 g HBr | 150° C., 60 min | 85 | 6 | 3.0 | 83 | 51.6 | 10.3 | 0.2 | 14.0 | 1.6 | 0.4 | 1.5 | 79.6 | 15.2 | 5.2 | bmimBr = butylmethylimidazolium bromide,
mim = methylimidizole,
TBABr = tetrabutyl ammonium bromide,
Ac = acetone,
IPA = isopropyl alcohol,
PA = propyl alcohol,
IPAc = isopropyl acetate,
PAc = propyl acetate,
IPBr = isopropyl bromide, TABLE 2-continued

| | Br-containing additive | Temp., time | Initial, mmol C3H8 | Initial, mmol O2 | Conv., % C3H8 | Conv., % O2 | Selectivity to C3, % Ac | IPA | PA | IPAc | PAc | IPBr | AAc | C3 | Sel. to other prod., % MAc + MA | COx |
|---|---|---|---|---|---|---|---|---|---|---|---|---|---|---|---|---|

AAc = acetol acetate,
C₃ = Ac + IPA + PA + IPAc + PAc + AAc + IPBr,
MAc = methyl acetate,
MA = methyl alcohol,
COx = CO₂ + CO.

TABLE 3

| | Composition [1] | Temperature, time | Initial, mmol C₃H₈ | Initial, mmol O₂ | Conv., % C₃H₈ | Conv., % O₂ | Sel. to C3, % Ac | IPA | PA | IPAc | PAc | C₃ | Sel. to other prod. % Mac + MA | Cox |
|---|---|---|---|---|---|---|---|---|---|---|---|---|---|---|
| 18 | 0.1 g NHPI, no other additives | 120° C., 30 min | 85 | 6 | 4.4 | 75 | 77.4 | 12.9 | 0.8 | 1.5 | 0.1 | 92.7 | 5.6 | 1.7 |
| 19 | 0.1 g NHPI, no other additives | 110° C., 20 min | 85 | 6 | 3.0 | 48 | 74.7 | 18.7 | 1.4 | 0.5 | <0.1 | 95.4 | 4.6 | <0.1 |
| 20 | 0.1 g NHPI, no other additives | 110° C., 20 min | 100 | 7 | 5.0 | 94 | 83.5 | 6.4 | 0.7 | 2.6 | 0.7 | 93.9 | 4.3 | 1.8 |
| 21 | 0.1 g NHPI, no other additives | 110° C., 20 min | 100 | 15.8 | 10 | 49 | 89.6 | 3.7 | 0.3 | 1.8 | 0.3 | 95.7 | 2.5 | 1.8 |
| 22 | 0.1 g NHPI, no other additives | 110° C., 20 min | 100 | 20.2 | 12.0 | 75 | 90.8 | 2.1 | 0.2 | 1.5 | 0.6 | 95.2 | 2.5 | 2.3 |
| 23 | 0.05 g NHPI, 1 g NaOAc | 120° C., 55 min | 85 | 6 | 4.5 | 77 | 79.7 | 10.8 | 0.6 | 2.2 | 0.1 | 93.4 | 5.8 | 0.8 |
| 24 | 0.05 g NHPI, 0.5 g MIm | 140° C., 20 min | 85 | 3 | 2.0 | 80 | 54.7 | 33.7 | 1.6 | 2.6 | <0.1 | 92.7 | 6.7 | 0.6 |
| 25 | 0.1 g NHPI, 1 g MIm | 150° C., 30 min | 85 | 3 | 2.1 | 83 | 64.4 | 15.8 | 0.3 | 8.2 | 0.6 | 89.3 | 6.2 | 4.5 |
| 26 | 0.1 g NHPI, 0.5 g MIm, 0.5 g H2O | 150° C., 50 min | 85 | 3 | 2.6 | 100 | 68.2 | 9.2 | 0.1 | 13.8 | 1.2 | 92.5 | 7.4 | <0.1 |
| 27 | 0.1 g NHPI, 0.1 g TBA(HSO4) | 135° C., 20 min | 85 | 6 | 5.4 | 98 | 73.8 | 14.3 | 1.3 | 2.7 | 0.2 | 92.3 | 6.1 | 1.6 |
| 28 | 0.1 g NHPI, 0.3 g H3BO3 | 120° C., 60 min | 85 | 6 | 1.2 | 25 | 58.5 | 26.4 | 1.7 | 2.3 | 0.1 | 89.0 | 10.9 | <0.1 |
| 29 | 0.05 g NHPI, 0.1 g H5PMo10V2O40 no Co(OAc)2 | 120° C., 100 min | 85 | 6 | 2.3 | 100 | 47.4 | 0.2 | 0.1 | 22.8 | 2.4 | 72.9 | 16.7 | 10.4 |
| 30 | 50% CH3CN, 0.1 g NHPI | 120° C., 23 min | 85 | 6 | 3.9 | 67 | 80.6 | 11.2 | 1.1 | 0.6 | 0.1 | 93.6 | 6.4 | <0.1 |
| 31 | 20% EAc, 0.1 g NHPI | 130° C., 20 min | 85 | 6 | 3.9 | 69 | 78.2 | 13.7 | 1.1 | 0.1 | 0.1 | 93.2 | 6.7 | <0.1 |
| 32 | 0.1 g NHPI, no other additives | 120° C., 30 min | 85 | 6 | 4.4 | 75 | 77.4 | 12.9 | 0.8 | 1.5 | 0.1 | 92.7 | 5.6 | 1.7 |

[1] HOAc, 0.1 g Co(OAc)₂, 5 mg TBHP, 50 ml of solution,
Abbreviations used:
NHPI = n-hydroxyphthalimide,
TBHP = tert-butyl hydroperoxide,
NaOAc = sodium acetate,
Mim = methylimidizole,
TBA(HSO₄) = tetrabutylammonium hydrogensulfate,
H₃BO₃ = boric acid,
H₅PMo₁₀V₂O₄₀ = a heterogeneous mixed metal oxide oxidation catalyst,
CH₃CN = acetonitrile,
EAc = ethylacetate,
Co(OAc)₂ = cobalt(II) acetate,
Ac = acetone,
IPA = isopropyl alcohol,
PA = propyl alcohol,
IPAc = isopropyl acetate,
PAc = propyl acetate,
C₃ = Ac + IPA + PA + IPAc + PAc,
MAc = methyl acetate,
MA = methyl alcohol, COx = CO₂ + CO.

TABLE 4

| No | T, time | Init., mmol C3H8 | Init., mmol O2 | Conv., % C3H8 | Conv., % O2 | Sel. To C3, % Ac | IPA | PA | IPAc | PAc | C3 | Sel. To other, % Mac + MA | Cox |
|---|---|---|---|---|---|---|---|---|---|---|---|---|---|
| 33 | 140°, 30 min | 84 | 15.3 | 3.2 | 19 | 71.2 | 20.3 | 0.3 | 1.0 | 0.1 | 92.9 | 6.4 | 0.7 |
| 34 | 140°, 49 min | 84 | 15.3 | 6.8 | 55 | 80.4 | 8.7 | 0.8 | 1.2 | 0.1 | 91.2 | 5.9 | 2.9 |
| 35 | 140°, 94 min | 84 | 15.3 | 6.7 | 49 | 82.8 | 8.2 | 0.9 | 1.0 | 0.2 | 93.1 | 3.8 | 3.1 |
| 36 | 140°, 60 min | 84 | 9.0 | 6.7 | 100 | 77.8 | 7.7 | 0.5 | 2.7 | 0.1 | 88.8 | 8.2 | 3.0 |

TABLE 4-continued

| No | T, time | Init., mmol | | Conv., % | | Sel. To C3, % | | | | | | Sel. To other, % | |
|---|---|---|---|---|---|---|---|---|---|---|---|---|---|
| | | C3H8 | O2 | C3H8 | O2 | Ac | IPA | PA | IPAc | PAc | C3 | Mac + MA | Cox |
| 37 | 140°, 47 min | 84 | 7.7 | 5.4 | 100 | 74.9 | 11.4 | 0.8 | 2.6 | 0.4 | 90.1 | 7.7 | 2.2 |
| 38 | 140°, 72 min | 84 | 6.5 | 7.7 | 62 | 81.5 | 5.5 | 0.7 | 2.4 | 0.3 | 90.4 | 5.0 | 4.6 |
| 39 | 140°, 67 min | 84 | 6.5 | 8.2 | 67 | 78.4 | 5.6 | 0.6 | 1.6 | 0.5 | 86.7 | 5.8 | 7.5 |

Ac = acetone,
IPA = isopropyl alcohol,
PA = propyl alcohol,
IPAc = isopropyl acetate,
PAc = propyl acetate,
$C_3$ = Ac + IPA + PA + IPAc + PAc,
MAc = methyl acetate,
MA = methyl alcohol,
COx = $CO_2$ + CO.

By the term "about", we mean within 10% of the value, or within 5%, or within 1%. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process comprising contacting a lower alkane, a solvent, a soluble metal catalyst, and a promoter in the presence of an oxidizing agent in a reaction zone under partial oxidation conditions to produce a partially oxidized product comprising one or more of a lower alkyl alcohol, a lower alkyl ketone, and a lower alkyl acetate, wherein a weight ratio of the lower alkane to oxygen is in a range of about 20:1 to about 1:2, wherein the soluble metal catalyst is a soluble metal salt of cobalt, manganese, chromium, titanium, copper, nickel, vanadium, iron, molybdenum, tin, cerium, zirconium, or combinations thereof, and wherein the promoter comprises a bromine source, an imide source, or combinations thereof. An embodiment of the invention is one, any or all of prior embodiments in this paragraph up through the first embodiment in this paragraph wherein the lower alkane comprises an alkane having 2 to 5 carbon atoms. An embodiment of the invention is one, any or all of prior embodiments in this paragraph up through the first embodiment in this paragraph wherein the solvent comprises a carboxylic acid, benzyl nitrile, acetonitrile, or combinations thereof. An embodiment of the invention is one, any or all of prior embodiments in this paragraph up through the first embodiment in this paragraph wherein the solvent comprises the carboxylic acid having from 1 to 7 carbon atoms. An embodiment of the invention is one, any or all of prior embodiments in this paragraph up through the first embodiment in this paragraph wherein the promoter comprises HBr, NaBr, KBr, $NH_4Br$, benzyl bromide, mono-bromoacetic acid, di-bromoacetic acid, bromoacetyl bromide, tetrabromoethane, ethylene dibromide, N-hydroxyphthalimide, or combinations thereof. An embodiment of the invention is one, any or all of prior embodiments in this paragraph up through the first embodiment in this paragraph wherein the soluble metal salt comprises at least one organic salt or inorganic salt of cobalt and at least one organic salt or inorganic salt of manganese. An embodiment of the invention is one, any or all of prior embodiments in this paragraph up through the first embodiment in this paragraph wherein a selectivity for the lower alkyl alcohol, the lower alkyl ketone, and the lower alkyl acetate is at least about 50%. An embodiment of the invention is one, any or all of prior embodiments in this paragraph up through the first embodiment in this paragraph wherein a selectivity for the lower alkyl alcohol, the lower alkyl ketone, and the lower alkyl acetate is at least about 70%. An embodiment of the invention is one, any or all of prior embodiments in this paragraph up through the first embodiment in this paragraph wherein the reaction conditions include at least one of a temperature in a range of about 40° C. to about 250° C., and a pressure in a range of about 0.7 MPa(g) to about 13.8 MPa(g). An embodiment of the invention is one, any or all of prior embodiments in this paragraph up through the first embodiment in this paragraph further comprising separating the partially oxidized product from the solvent. An embodiment of the invention is one, any or all of prior embodiments in this paragraph up through the first embodiment in this paragraph wherein the oxidizing agent comprises an oxygen-containing gas, peroxides, superoxides, nitrogen compounds containing oxygen, or combinations thereof. An embodiment of the invention is one, any or all of prior embodiments in this paragraph up through the first embodiment in this paragraph further comprising separating the partially oxidized product from unreacted lower alkane; and recycling the unreacted lower alkane to the reaction zone.

A second embodiment of the invention is a process comprising contacting a lower alkane, a solvent, a soluble metal catalyst, and a promoter in the presence of an oxidizing agent in a reaction zone under partial oxidation conditions to produce a partially oxidized product comprising one or more of a lower alkyl alcohol, a lower alkyl ketone, and a lower alkyl acetate, wherein the catalyst comprises a soluble metal salt of cobalt, manganese, chromium, titanium, copper, nickel, vanadium, iron, molybdenum, tin, cerium, zirconium, or combinations thereof, wherein the promoter comprises a bromine source, an imide source, or combinations thereof, wherein the lower alkane comprises an alkane having 2 to 5 carbons, wherein a weight ratio of the lower alkane to oxygen is in a range of about 20:1 to about 1:2, and wherein the reaction conditions include a temperature in a range of about 40° C. to about 250° C., and a pressure in a range of about 0.7 MPa(g) to about 13.8 MPa(g). An embodiment of the invention is one, any or all of prior embodiments in this paragraph up through the second embodiment in this paragraph wherein the solvent comprises a carboxylic acid having 1 to 7 carbon atoms, benzyl nitrile, acetonitrile, or combinations thereof. An embodiment of the invention is one, any or all of prior embodiments in this paragraph up through the second embodiment in this paragraph wherein the promoter comprises HBr, NaBr, KBr, $NH_4Br$, benzyl bromide, monobromoacetic acid, dibromoacetic acid, bromoacetylbromide, tetrabromoethane, ethylene dibromide, N-hydroxyphthalimide, or combinations thereof. An embodiment of the invention is one, any or all of prior embodiments in this paragraph up through the second embodiment in this paragraph wherein a selectivity for the lower alkyl alcohol, the lower alkyl ketone, and the lower alkyl acetate is at least about 50%. An embodiment of the invention is one, any or all of prior embodiments in this paragraph up through the second embodiment in this paragraph wherein a selectivity for the lower alkyl alcohol, the lower alkyl ketone, and the lower alkyl acetate is at least about 70%. An embodiment of the invention is one, any or all of prior embodiments in this paragraph up through the second embodiment in this paragraph further comprising separating the partially oxidized product from the solvent. An embodiment of the invention is one, any or all of prior embodiments in this paragraph up through the second embodiment in this paragraph wherein the oxidizing agent comprises an oxygen-containing gas, peroxides, superoxides, nitrogen compounds containing oxygen, or combinations thereof. An embodiment of the invention is one, any or all of prior embodiments in this paragraph up through the second embodiment in this paragraph further comprising separating the partially oxidized product from unreacted lower alkane; and recycling the unreacted lower alkane to the reaction zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A liquid phase selective oxidation process comprising contacting a lower alkane, a solvent, a soluble metal catalyst, and a promoter in the presence of an oxidizing agent in a reaction zone under partial oxidation conditions to selectively produce a partially oxidized product comprising one or more of a lower alkyl alcohol, a lower alkyl ketone, and a lower alkyl acetate, wherein a weight ratio of the lower alkane to oxygen present in the oxidizing agent is in a range of about 50:1 to about 7:1, wherein the soluble metal catalyst is a soluble metal salt and the metal consists essentially of one metal selected from the group of cobalt, manganese, chromium, titanium, copper, nickel, vanadium, iron, molybdenum, tin, cerium, and zirconium, wherein the process has less than 10% selectivity to CO and $CO_2$, and wherein the promoter comprises a bromine source, an imide source, or combinations thereof.

2. The process of claim 1 wherein the lower alkane comprises an alkane having 2 to 5 carbon atoms.

3. The process of claim 1 wherein the solvent comprises a carboxylic acid, benzyl nitrile, acetonitrile, or combinations thereof.

4. The process of claim 3 wherein the solvent comprises the carboxylic acid and the carboxylic acid has from 1 to 7 carbon atoms.

5. The process of claim 1 wherein the promoter comprises HBr, NaBr, KBr, $NH_4Br$, benzyl bromide, mono-bromoacetic acid, di-bromoacetic acid, bromoacetyl bromide, tetrabromoethane, ethylene di-bromide, N-hydroxyphthalimide, or combinations thereof.

6. The process of claim 1 wherein a selectivity for the lower alkyl alcohol, the lower alkyl ketone, and the lower alkyl acetate is at least about 50%.

7. The process of claim 1 wherein a selectivity for the lower alkyl alcohol, the lower alkyl ketone, and the lower alkyl acetate is at least about 70%.

8. The process of claim 1 wherein the reaction conditions include at least one of: a temperature in a range of about 40° C. to about 250° C., and a pressure in a range of about 0.7 MPa(g) to about 13.8 MPa(g).

9. The process of claim 1 further comprising separating the partially oxidized product from the solvent.

10. The process of claim 1 wherein the oxidizing agent comprises an oxygen-containing gas, peroxides, superoxides, nitrogen compounds containing oxygen, or combinations thereof.

11. The process of claim 1 further comprising separating the partially oxidized product from unreacted lower alkane and recycling the unreacted lower alkane to the reaction zone.

12. A liquid phase selective oxidation process comprising contacting a lower alkane, a solvent, a soluble metal catalyst, and a promoter in the presence of an oxidizing agent in a reaction zone under partial oxidation conditions to selectively produce a partially oxidized product comprising one or more of a lower alkyl alcohol, a lower alkyl ketone, and a lower alkyl acetate, wherein the catalyst comprises a soluble metal salt and the metal consists essentially of one metal selected from the group of cobalt, manganese, chromium, titanium, copper, nickel, vanadium, iron, molybdenum, tin, cerium, and zirconium, wherein the process has less than 10% selectivity to CO and $CO_2$, wherein the promoter comprises a bromine source, an imide source, or combinations thereof, wherein the lower alkane comprises an alkane having 2 to 5 carbons, wherein a weight ratio of the lower alkane to oxygen present in the oxidizing agent is in a range of about 50:1 to about 7:1, and wherein the reaction conditions include a temperature in a range of about 40° C. to about 250° C., and a pressure in a range of about 0.7 MPa(g) to about 13.8 MPa(g).

13. The process of claim 12 wherein the solvent comprises a carboxylic acid having 1 to 7 carbon atoms, benzyl nitrile, acetonitrile, or combinations thereof.

14. The process of claim 12 wherein the promoter comprises HBr, NaBr, KBr, $NH_4Br$, benzyl bromide, monobromoacetic acid, dibromoacetic acid, bromoacetylbromide, tetrabromoethane, ethylene dibromide, N-hydroxyphthalimide, or combinations thereof.

15. The process of claim 12 wherein a selectivity for the lower alkyl alcohol, the lower alkyl ketone, and the lower alkyl acetate is at least about 50%.

16. The process of claim 12 wherein a selectivity for the lower alkyl alcohol, the lower alkyl ketone, and the lower alkyl acetate is at least about 70%.

17. The process of claim 12 further comprising separating the partially oxidized product from the solvent.

18. The process of claim 12 wherein the oxidizing agent comprises an oxygen-containing gas, peroxides, superoxides, nitrogen compounds containing oxygen, or combinations thereof.

19. The process of claim 12 further comprising separating the partially oxidized product from unreacted lower alkane and recycling the unreacted lower alkane to the reaction zone.

* * * * *